US010281592B2

United States Patent
Kawata et al.

(10) Patent No.: US 10,281,592 B2
(45) Date of Patent: May 7, 2019

(54) RADIATION MEASURING APPARATUS, COMPUTER PROGRAM PRODUCT, AND RADIATION COMPUTED TOMOGRAPHY APPARATUS

(71) Applicant: Canon Medical Systems Corporation, Otawara-shi (JP)

(72) Inventors: Go Kawata, Kawasaki (JP); Shunsuke Kimura, Kawasaki (JP); Hideyuki Funaki, Shinagawa (JP); Masanori Furuta, Odawara (JP); Tetsuro Itakura, Nerima (JP)

(73) Assignee: Canon Medical Systems Corporation, Otawara-shi (JP)

( * ) Notice: Subject to any disclaimer, the term of this patent is extended or adjusted under 35 U.S.C. 154(b) by 167 days.

(21) Appl. No.: 15/257,182

(22) Filed: Sep. 6, 2016

(65) Prior Publication Data

US 2016/0370475 A1 Dec. 22, 2016

Related U.S. Application Data

(63) Continuation of application No. PCT/JP2015/057204, filed on Mar. 11, 2015.

(30) Foreign Application Priority Data

Mar. 24, 2014 (JP) ................. 2014-060263

(51) Int. Cl.
  *A61B 6/00* (2006.01)
  *A61B 6/03* (2006.01)
  *G01T 1/17* (2006.01)

(52) U.S. Cl.
  CPC ............... *G01T 1/17* (2013.01); *A61B 6/032* (2013.01); *A61B 6/4241* (2013.01); *A61B 6/482* (2013.01); *A61B 6/542* (2013.01)

(58) Field of Classification Search
  CPC ....... A61B 6/032; A61B 6/4241; A61B 6/482; A61B 6/542; G01T 1/17; G01T 1/172; G01T 1/18
  See application file for complete search history.

(56) References Cited

U.S. PATENT DOCUMENTS

| 3,717,753 A * | 2/1973 | Thomas ................ G01T 1/2045 250/306 |
| 2002/0109091 A1* | 8/2002 | Overdick ............ G01N 23/046 250/336.1 |
| 2009/0140159 A1 | 6/2009 | Tomita et al. |

FOREIGN PATENT DOCUMENTS

| JP | 1-118393 U | 8/1989 |
| JP | 4-270986 A | 9/1992 |

(Continued)

OTHER PUBLICATIONS

English translation of the Written Opinion dated Apr. 7, 2015 in PCT/JP2015/057204 filed Mar. 11, 2015.

(Continued)

*Primary Examiner* — Chih-Cheng Kao
(74) *Attorney, Agent, or Firm* — Oblon, McClelland, Maier & Neustadt, L.L.P.

(57) ABSTRACT

According to an embodiment, a radiation measuring apparatus includes a detector, comparators, a threshold controller, counters, and a generator. The detector includes plural detecting elements each configured to convert energy of incident radiation into a first electrical signal. The comparators correspond to the respective detecting elements, each comparator being configured to output a second electrical signal when a level of the corresponding first electrical signal is not less than a threshold. The threshold controller is configured to supply a first value as the threshold to the respective comparators at a first time, and supply a second value as the threshold to the respective comparators at a (Continued)

second time. The counters correspond to the respective comparators, each counter being configured to count the corresponding second electrical signal. The generator is configured to generate a pulse height frequency distribution of the radiation by using counts of the counters.

7 Claims, 10 Drawing Sheets

(56) References Cited

FOREIGN PATENT DOCUMENTS

| JP | 2000-69369 A | 3/2000 |
|---|---|---|
| JP | 2007-256096 | 10/2007 |
| JP | 2009-14624 A | 1/2009 |
| JP | 2013-88317 A | 5/2013 |
| JP | 2013-88319 A | 5/2013 |

OTHER PUBLICATIONS

International Search Report (with English translation) dated Apr. 7, 2015 in PCT/JP2015/057204 filed on Mar. 11, 2015.
Written Opinion dated Apr. 7, 2015 in PCT/JP2015/057204 filed on Mar. 11, 2015.

\* cited by examiner

FIG.9

MEASUREMENT CALIBRATION MODE
↓
ACQUIRE DATA OUTPUT BY FPGA AND OUTPUT DATA IN PREDETERMINED DATA FORMAT — S1
↓
PERFORM DATA VALIDATION PROCESS, AND DISPLAY PULSE HEIGHT HISTOGRAM — S2
↓
CALCULATE PARAMETER BY SMOOTHING — S3

FIG.10

|  | COUNT RATE (COUNT/NUMBER OF CLOCKS) |
|---|---|
| $Vth\_1$ | Count Rate_1 |
| $Vth\_2$ | Count Rate_2 |
| ⋮ | ⋮ |
| $Vth\_n$ | Count Rate_n |

|  | COUNT RATE |
|---|---|
| Vth_1 | Count Rate_1 |
| Vth_2 | Count Rate_2 |
| ⋮ | ⋮ |
| Vth_n | Count Rate_n |

RADIATION MEASURING APPARATUS, COMPUTER PROGRAM PRODUCT, AND RADIATION COMPUTED TOMOGRAPHY APPARATUS

CROSS-REFERENCE TO RELATED APPLICATION

This application is a continuation of PCT international Application Ser. No. PCT/JP2015/057204, filed on Mar. 11, 2015, which designates the United States; the entire contents of which are incorporated herein by reference.

FIELD

Embodiments described herein relate generally to a radiation measuring apparatus, a computer program product, and a radiation computed tomography apparatus.

BACKGROUND

At present, radiation detection techniques including a direct conversion technique and an indirect conversion technique are known. In the direct conversion technique, pulse height of the output is proportional to the energy of incident radiation are output. In the indirect conversion technique, fluorescence produced when radiation is incident on a scintillator is detected by a photodiode, a photomultiplier element, and the like.

In the indirect conversion technique, a scintillator has a property that the number of fluorescence photons emitted by the phosphor is proportional to the radiation energy incident on the phosphor. Thus, counting the number of fluorescence photons emitted by a phosphor enables measurement of the energy of radiation having passed through a subject. This property can be applied to a computed tomography (CT) system and the like to acquire a CT image through energy discrimination, for example, and allow material decomposition on the CT image. Furthermore, if y-ray energy emitted when a radioactive isotope disintegrates can be detected, a spatial distribution of radioactive isotopes dispersed on the ground, for example, can be obtained.

In radiation energy decomposition in combination of a scintillator and a photon detector, for energy discrimination through calculation of the number of fluorescence photons emitted by the scintillator, the output pulse generated by detection of a radiation need to be integrated for a predetermined time.

In development of radiation measuring apparatuses based on a technique (photon counting technique) of measuring radiation photons in a single photon region and analyzing the energy of the radiation photons, higher count rates of detecting elements and highly accurate energy decomposition are desired.

In the conventional technique, pulses having pulse heights proportional to radiation energy are generated, a plurality of comparators having thresholds corresponding to the number of decomposition stages are set for the pulse heights corresponding to the radiation energy are provided, and the comparators measure the frequencies of occurrence of pulses with the respective thresholds to form a histogram for radiation energy.

With the conventional technique, however, comparators, the number of which is proportional to the required number of energy decomposition stages, need to be implemented, which is an obstruction to increasing the density and reducing the power consumption of radiation measuring apparatuses.

BRIEF DESCRIPTION OF THE DRAWINGS

FIG. 9 is a flowchart illustrating a process flow in a measurement calibration mode;

FIG. 10 is a table illustrating an example of data strings of combinations of a measurement signal threshold and a count rate;

DETAILED DESCRIPTION

According to an embodiment, a radiation measuring apparatus includes a detector, a plurality of comparators, a threshold controller, a plurality of counters, and a pulse height frequency distribution generator. The detector includes a plurality of detecting elements each configured to convert energy of incident radiation into a first electrical signal. The comparators correspond to the respective detecting elements, each comparator being configured to output a second electrical signal when a level of the corresponding first electrical signal is higher than or equal to a threshold. The threshold controller is configured to supply a first value as the threshold to the respective comparators at a first time, and supply a second value as the threshold to the respective comparators at a second time different from the first time. The counters correspond to the respective comparators, each counter being configured to count the corresponding second electrical signal. The pulse height frequency distribution generator is configured to generate a pulse height frequency distribution of the radiation by using counts of the counters.

Hereinafter, a photon counting CT system according to embodiments to which a radiation measuring apparatus and a radiation measurement program are applied will be described in detail with reference to the drawings.

First Embodiment

A photon counting CT system of a first embodiment counts photons from X-rays (X-ray photons) having passed through a subject by using a photon counting detector to reconstruct X-ray CT image data having a high SNR. Individual photons have different energies. The photon counting CT system measures energy levels of photons to obtain information on X-ray energy components. The photon counting CT system divides projection data, which have been collected by driving X-ray tubes at one tube voltage, into a plurality of energy components to form an image.

Figure 1:
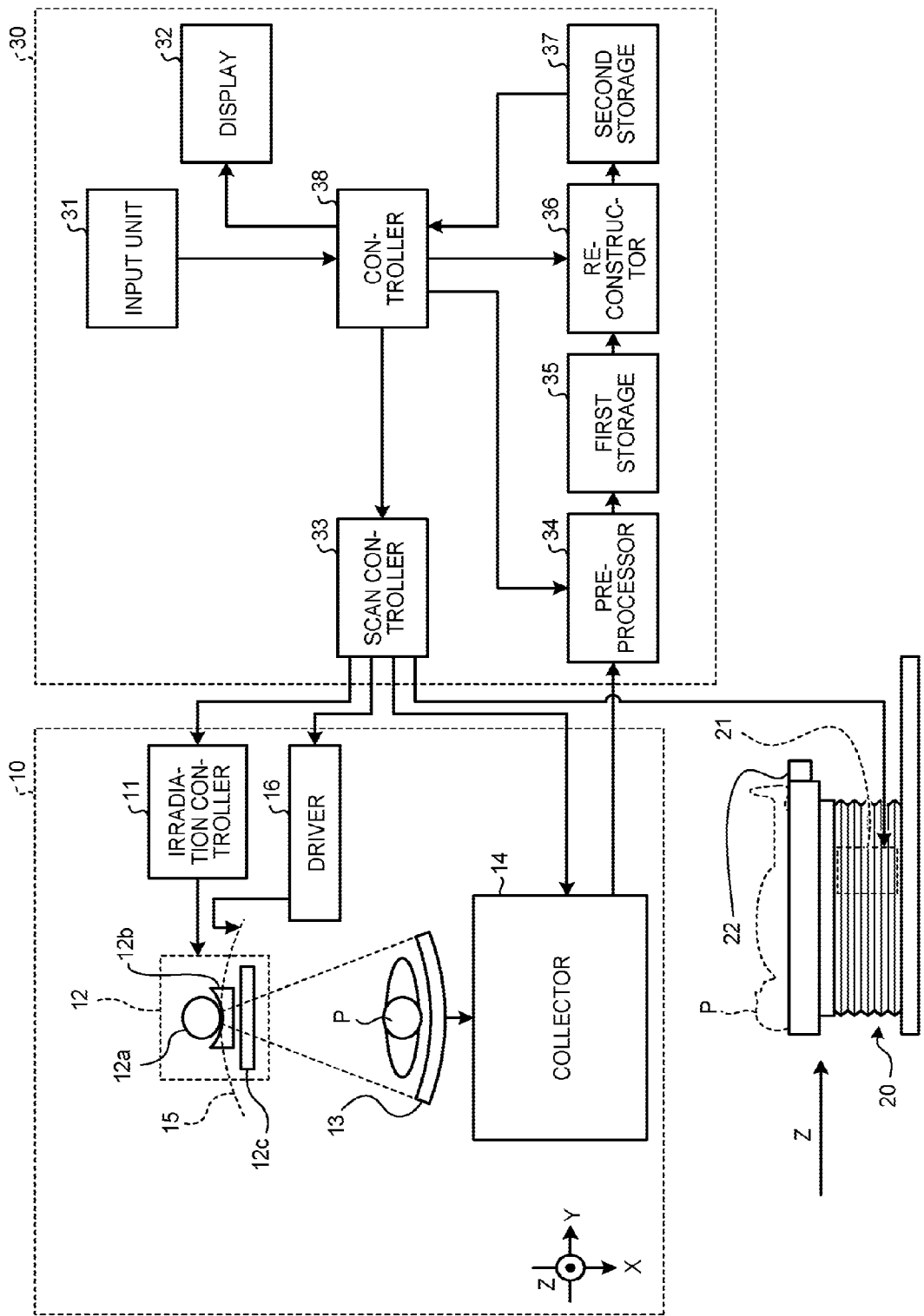
FIG. 1 is a diagram illustrating a configuration of a photon counting CT system of a first embodiment.

FIG. 1 illustrates a configuration of the photon counting CT system of the first embodiment. As illustrated in FIG. 1, the photon counting CT system includes a gantry 10, a bed 20, and a console 30.

The gantry 10 includes an irradiation controller 11, an X-ray generator 12, a detector 13, a collector (DAS: data acquisition system) 14, a rotatable frame 15, and a driver 16. The gantry 10 emits X-rays to a phantom P, and counts the number of X-rays having passed through the phantom P (or a subject).

The rotatable frame 15 supports the X-ray generator 12 and the detector 13 so that the X-ray generator 12 and the detector 13 are opposed to each other with the phantom P therebetween. The rotatable frame 15 is an annular frame rotated at a high speed along a circular path around the phantom P by the driver 16, which will be described later.

The X-ray generator 12 includes an X-ray tube 12a, a wedge 12b, and a collimator 12c. The X-ray generator 12 is a device for emitting X-rays to the phantom P. The X-ray tube 12a is a vacuum tube for emitting X-rays to the phantom P by using high voltage supplied from the X-ray generator 12, which will be described later. The X-ray tube 12a emits X-ray beams to the phantom P while rotating with the rotation of the rotatable frame 15. The X-ray tube 12a generates X-ray beams spreading at a fan angle and a cone angle.

The wedge 12b is an X-ray filter for adjusting the amount of X-rays emitted from the X-ray tube 12a. Specifically, the wedge 12b is a filter that transmits and attenuates X-rays emitted from the X-ray tube 12a to the phantom P so that the distribution of the X-rays emitted from the X-ray tube 12a becomes a predetermined distribution.

For example, the wedge 12b is a filter made by processing aluminum to have a predetermined target angle and a predetermined thickness. Note that the wedge is also called a wedge filter or a bow-tie filter. The collimator 12c is a slit for narrowing the emission range of X-rays whose amount is adjusted by the wedge 12b under the control of the irradiation controller 11, which will be described later.

The irradiation controller 11 is a device serving as a high voltage generator to supply a high voltage to the X-ray tube 12a, and the X-ray tube 12a uses the high voltage supplied from the irradiation controller 11 to generate X-rays. The irradiation controller 11 adjusts a tube voltage and a tube current to be supplied to the X-ray tube 12a to adjust the amount of X-rays emitted to the phantom P. The irradiation controller 11 also adjusts the aperture of the collimator 12c to adjust the X-ray emission range (the fan angle and the cone angle).

The driver 16 rotates the rotatable frame 15 to cause the X-ray generator 12 and the detector 13 to rotate along a circular path around the phantom P. Each time an X-ray photon enters the detector 13, the detector 13 outputs a signal allowing measurement of the energy level of the X-ray photon. The X-ray photons are, for example, X-ray photons emitted from the X-ray tube 12a and passing through the phantom P. The detector 13 includes a plurality of detecting elements, each of which outputs a one-pulse electrical signal (analog signal) each time an X-ray photon enters the detecting element. The number of X-ray photons having entered each detecting element can be counted by counting the number of electrical signals (pulses). Furthermore, the energy level of an X-ray photon that caused a signal to be output can be measured through predetermined computation on the signal.

The detecting elements of the detector 13 are constituted by scintillators and photosensors such as photomultiplier elements (SiPM: Silicon Photomultipliers). The detector 13 is what is called an "indirect-conversion detector". The detector 13 first converts X-ray photons incident thereon into scintillation light by the scintillators, and then converts the scintillation light into electrical signals by the photosensors such as photomultiplier elements. While what is called an "indirect-conversion detector" is provided as the detector 13 in this example, "direct-conversion detector" that directly acquires charge pulses corresponding to the amount of X-rays incident thereon without using a scintillator or the like may alternatively be provided.

Figure 2:
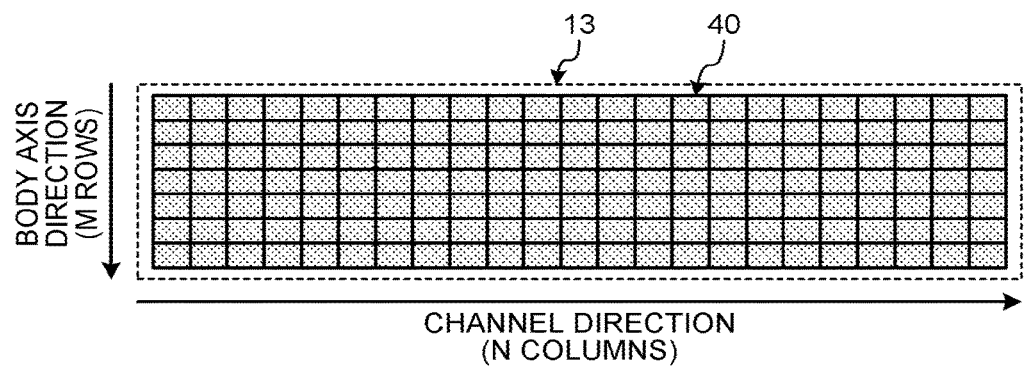
FIG. 2 is a plan view of a detector provided in the photon counting CT system of the first embodiment.

FIG. 2 illustrates an example of the detector 13. The detector 13 is an area detector in which the detecting elements 40 constituted by scintillators and photosensors such as photomultiplier elements are arranged in N columns in a channel direction (in a Y-axis direction in FIG. 1) and M rows in a body axis direction (in a Z-axis direction in FIG. 1). The detecting elements 40 each output a one-pulse electrical signal when a photon is incident on the detecting element 40. Individual pulses output by the detecting elements 40 are discriminated from one another, which enables counting of the number of X-ray photons incident on the detecting elements 40. In addition, measurement of the energy levels of the counted X-ray photons can be performed by computation based on the intensities of the pulses.

Note that a circuit called an analog front end, which counts the outputs of the detecting elements 40 and supplies the counted result to the collector 14 illustrated in FIG. 1, is provided downstream of the detector 13.

The collector 14 collects count information, which is the result of counting the outputs of the detector 13. Thus, the collector 14 discriminates individual signals output from the detector 13 and collects the count information. The count information is information collected from individual signals output by the detector 13 (the detecting elements 40) each time an X-ray photon having been emitted from the X-ray tube 12a and having passed through the subject P enters the detector 13. Specifically, the count information is information including a count and an energy level, which are associated with each other, of the X-ray photons incident on the detector 13 (the detecting elements 40). The collector 14 transmits the collected count information to the console 30.

Specifically, the collector 14 collects incidence positions (detected positions) of the X-ray photons counted by discriminating the respective pulses output by the detecting elements 40 and the energy levels of the X-ray photons as the count information at each phase (tube phase) of the X-ray tube 12a. The collector 14 uses positions of the detecting elements 40 that have output pulses (electrical signals) used in counting as the incidence positions, for example. The collector 14 performs predetermined computation on the electrical signals to measure the energy levels of the X-ray photons.

Next, the bed 20 illustrated in FIG. 1 is an apparatus on which a subject P is placed, and includes a top table 22 and a bed driving device 21. The top table 22 is a board on which a subject P is placed, and the bed driving device 21 moves the top table 22 in the Z-axis direction to move the subject P into the rotatable frame 15.

Note that the gantry 10 performs helical scan of helically scanning the subject P by rotating the rotatable frame 15 while moving the top table 22, for example. Alternatively, the gantry 10 performs conventional scan of scanning the subject P along a circular path by rotating the rotatable frame 15 with the position of the subject P being fixed after moving the top table 22. Alternatively, the gantry 10 performs conventional scan in a step-and-shoot method of performing conventional scan in a plurality of scan areas by moving the position of the top table 22 at regular intervals.

Next, the console 30 has functions of an input unit 31, a display 32, a scan controller 33, a preprocessor 34, a first storage 35, a reconstructor 36, a second storage 37, and a controller 38. The console 30 receives operation of the photon counting CT system made by an operator, and uses the counting information collected by the gantry 10 to reconstruct an X-ray CT image.

The input unit 31 transfers information on various instructions and various settings input by the operator of the photon counting CT system through operation of a mouse, a keyboard or the like to the controller 38. For example, the input unit 31 receives a condition on imaging of X-ray CT image data, a reconstruction condition in reconstruction of X-ray CT image data, a condition on image processing of X-ray CT image data, and the like from the operator.

The display 32 is a monitor viewed by the operator, and displays X-ray CT image data and a GUI (Graphical User Interface) for receiving various instructions, settings, and the like from the operator via the input unit 31 under the control of the controller 38.

The scan controller 33 controls the operations of the irradiation controller 11, the driver 16, the collector 14, and the bed driving device 21 under the control of the controller 38 to control the process of collecting the count information in the gantry 10.

The preprocessor 34 performs correction processes such as a logarithmic transformation process, offset correction, sensitivity correction, and beam hardening correction on the count information sent from the collector 14 to generate projection data.

The first storage 35 stores the projection data generated by the preprocessor 34. Specifically, the first storage 35 stores the projection data (corrected counting information) for reconstructing X-ray CT image data.

The reconstructor 36 uses the projection data stored in the first storage 35 to reconstruct X-ray CT image data. There are various methods for reconstruction, including back projection. Examples of the back projection include back projection according to the FBP (Filtered Back Projection) technique. The reconstructor 36 also performs various image processing on the X-ray CT image data to generate image data. The reconstructor 36 stores the reconstructed X-ray CT image data and the image data generated through the image processing into the second storage 37.

Note that the projection data generated from the count information acquired by the photon counting CT system contain information on the energy of X-rays reduced as a result of passing through the subject P. The reconstructor 36 is thus capable of reconstructing X-ray CT image data of a specific energy component, for example. The reconstructor 36 is also capable of reconstructing X-ray CT image data of each of a plurality of energy components, for example.

The reconstructor 36 is also capable of generating a plurality of X-ray CT image data that are color-coded according to energy components by assigning a tone corresponding to the energy component to each pixel of X-ray CT image data of respective energy components, and further generating image data on which the X-ray CT image data are superimposed.

The controller 38 controls the operations of the gantry 10, the bed 20, and the console 30 to control the whole photon counting CT system. Specifically, the controller 38 controls the scan controller 33 to control CT scan performed by the gantry 10. The controller 38 also controls the preprocessor 34 and the reconstructor 36 to control an image reconstruction process and an image generation process performed by the console 30. The controller 38 also controls display of various image data stored in the second storage 37 onto the display 32.

Figure 3:
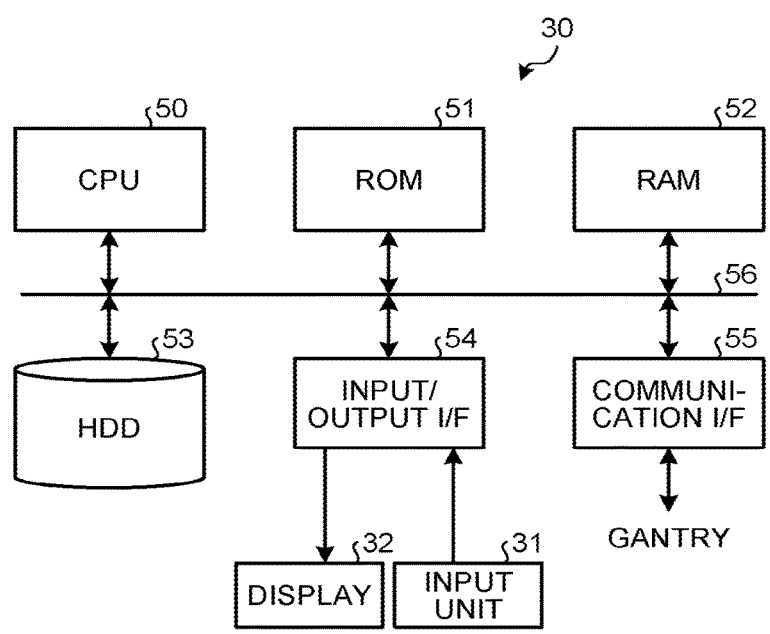
FIG. 3 is a hardware configuration diagram of the photon counting CT system of the first embodiment.

Next, FIG. 3 illustrates a hardware configuration diagram of the console 30. As illustrated in FIG. 3, the console 30 has a hardware configuration similar to that of a common personal computer. Specifically, the console 30 includes a CPU 50, a ROM 51, a RAM 52, an HDD 53, an input/output I/F 54, and a communication I/F 55. The input unit 31 and the display 32 described above are connected to the input/output I/F 54. CPU stands for "Central Processing Unit". ROM stands for "Read Only Memory". RAM stands for "Random Access Memory". HDD stands for "Hard Disk Drive". I/F stands for "Interface".

The CPU 50 to the communication I/F 55 are connected with one another via a bus line 56. The communication I/F 55 is connected to the gantry 10. The CPU 50 acquires X-ray image data and the like collected by the collector 14 via the communication I/F 55. The scan controller 33, the preprocessor 34, the reconstructor 36, or the controller 38 may be implemented by software in such a manner that the CPU 50 functions according to a program, or may be partly or entirely implemented by hardware. The ROM 51, the RAM 52, and the HDD 53 corresponds to the first storage 35 or the second storage 37.

Next, the photon counting CT system of the first embodiment is provided with one comparator for each one output pulse of the detector 13, and is configured to update the thresholds of the comparators at every measurement time to measure the frequencies of occurrence of pulses with the thresholds and generate a pulse height frequency distribution of outputs of the detector 13 in response to radiation incidence. Such an operation of generating a pulse height frequency distribution is executed by the CPU 50 operating according to a radiation measurement program stored in the HDD 53, the ROM 51, or the RAM 52 illustrated in FIG. 3.

Note that the radiation measurement program may be recorded on a computer-readable recording medium, which may be provided as a computer program product, such as a CD-ROM or a flexible disk (FD) in a form of a file that can be installed or executed and provided therefrom. Alternatively, the radiation measurement program may be recorded on a computer-readable recording medium such as a CD-R, a DVD, or a semiconductor memory and provided therefrom. DVD stands for "Digital Versatile Disk". Still alternatively, the radiation measurement program may be provided via a network such as the Internet, and the photon counting CT system may download and store the radiation measurement program via the network into a storage such as the ROM 51, the RAM 52 or the HDD 53 for execution. Still alternatively, the radiation measurement program may be embedded in a ROM or the like in the photon counting CT system in advance and provided therefrom.

Figure 4:
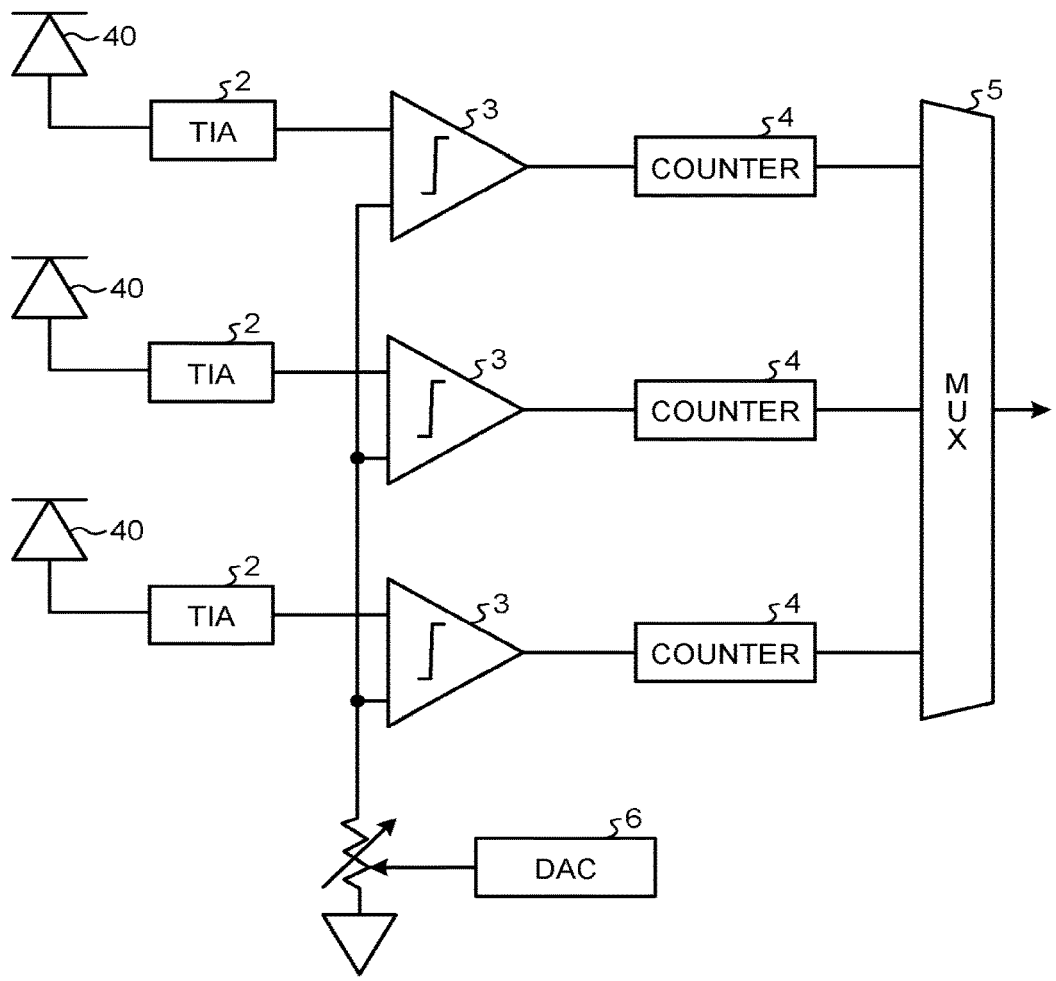
FIG. 4 is a block diagram of an analog front end of the detector provided in the photon counting CT system of the first embodiment.

FIG. 4 is a block diagram of the analog front end provided at an output of the detector 13. As illustrated in FIG. 4, the detector 13 includes pre-amplifiers (TIA: Transimpedance Amplifiers) 2, which amplify radiation signals detected by the detecting elements 40 with a predetermined gain, in a part of the analog front end. The detector 13 also includes comparators 3, counters 4, a multiplexer 5, and a threshold generator 6.

Figure 5:
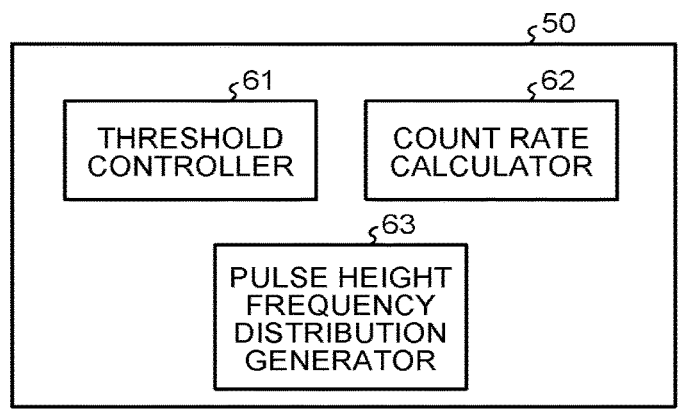
FIG. 5 is a functional block diagram of the photon counting CT system of the first embodiment.

FIG. 5 is a block diagram of functions of the CPU 50 implemented by operations according to the radiation measurement program. The CPU 50 operates according to the radiation measurement program to function as a threshold controller 61, a count rate calculator 62, and a pulse height frequency distribution generator 63. While the threshold controller 61, the count rate calculator 62, and the pulse height frequency distribution generator 63 are assumed to be implemented by software by the CPU 50, some or all of these functions may alternatively be implemented by hardware.

One threshold generator 6 is provided for all of the detecting elements 40 of the detector 13 (one threshold generator 6 for all the channels). Alternatively, one threshold generator 6 may be provided for a plurality of detecting elements 40, such as one threshold generator 6 for ten detecting elements 40 or for thirty detecting elements 40.

Figure 6:
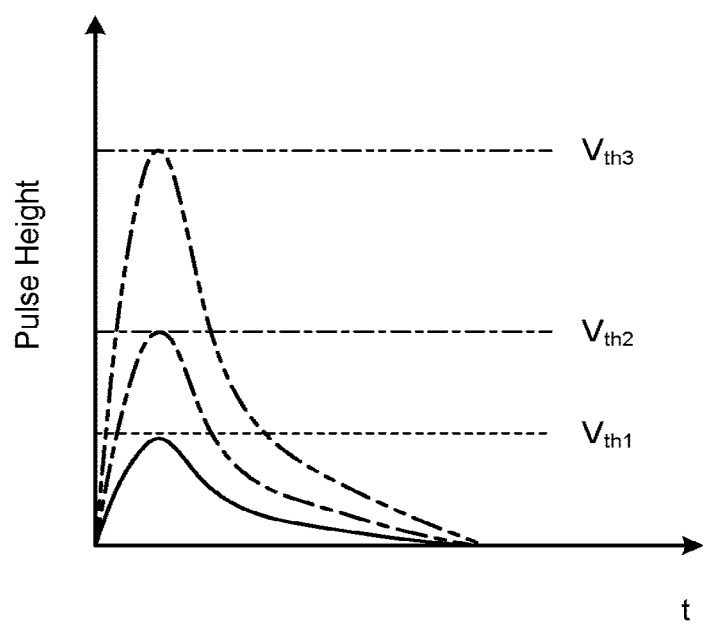
FIG. 6 is a graph illustrating an example of thresholds set and updated in comparators in the photon counting CT system of the first embodiment.

The threshold generator 6 supplies threshold signals having the same voltage to the respective comparators 3. The threshold generator 6 also changes the voltage of the threshold signals to be supplied to the comparators 3 at every predetermined time. Thus, threshold data, which are digital data whose values are changed at every predetermined time, are supplied to the threshold generator 6 from the threshold controller 61. The threshold generator 6 generates the threshold signals by converting the threshold data into analog data, and supplies the threshold signals to the respective comparators 3. In FIG. 6, the horizontal axis is a time axis, the vertical axis represents the pulse height of an X-ray detection signal, the dotted line represents threshold data $V_{th1}$, the long dashed short dashed line represents threshold data $V_{th2}$, and the long dashed double-short dashed line represents thresholds $V_{th3}$. Thresholds updated at every unit time are supplied to the respective comparators 3 as illustrated by the threshold data $V_{th1}$, the threshold data $V_{th2}$, and the threshold data $V_{th3}$ in FIG. 6.

The comparators 3 output pulses when X-ray signals equal to or higher than the threshold signals supplied from the threshold generator 6 are supplied. As described above, the values of the threshold signals supplied to the comparators 3 are updated at every unit time. The comparators 3 thus compare the threshold signals whose values are updated at every unit time and the X-ray signals from the detecting elements 40 to output pulses.

The counters 4 count the numbers of pulses from the comparators 3. The multiplexer 5 selects the count signals from the comparators 3 and supplies the selected count signals to a subsequent circuit. The count rate calculator 62 and the pulse height frequency distribution generator 63 use the count signals supplied via the counters 4 and the multiplexer 5 to measure correlation between the frequencies of pulses output from the comparators 3 and the threshold signals for pulse heights analysis.

Figure 7A:
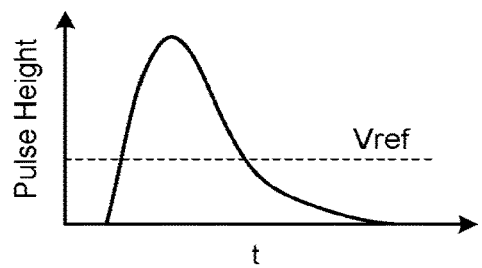
FIG. 7A is a graph for explaining the principle of X-ray measurement in the photon counting CT system of the first embodiment, and illustrating the relation between a predetermined threshold Vref and an X-ray signal.
Figure 7B:
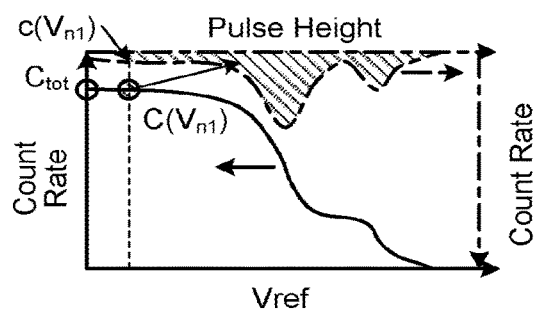
FIG. 7B is a graph for explaining the principle of X-ray measurement in the photon counting CT system of the first embodiment, and illustrating a relation between an updated threshold (horizontal axis: Vref) and a count of an X-ray signal (vertical axis: Count Rate)
Figure 7C:
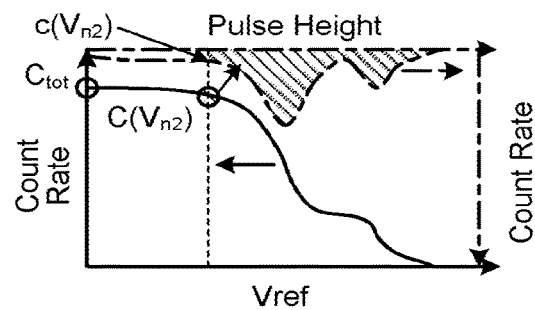
FIG. 7C is a graph for explaining the principle of X-ray measurement in the photon counting CT system of the first embodiment, and illustrating another relation between an updated threshold (horizontal axis: Vref) and a count of an X-ray signal (vertical axis: Count Rate)

FIGS. 7A to 7C are graphs for explaining the principle of X-ray measurement in the photon counting CT system of the embodiment. FIG. 7A is a graph illustrating the relation between a given threshold Vref and X-ray signals. FIG. 7B is a graph illustrating a relation between an updated threshold (the horizontal axis: Vref) and a count of an X-ray signal (the vertical axis: Count Rate). FIG. 7C is a graph illustrating another relation between an updated threshold (the horizontal axis: Vref) and a count of an X-ray signal (the vertical axis: Count Rate). In a case where the count rate of an X-ray signal is defined as "count actual measurement time", the detection frequency of the X-ray signal lowers as the value of the threshold is larger as illustrated in the graphs illustrating codes in FIGS. 7B and 7C. This phenomenon can be understood on the basis of the fact that the count (count rate) of radiation signals equal to or higher than a given threshold is given by a difference between a net count and a count of radiation signals lower than the given threshold. Thus, detection of a difference between a count rate obtained with a first threshold of a given value and a count rate obtained with a second threshold of a value different from that of the first threshold allows the detection frequency of radiation signals for each pulse height to be constructed.

Specifically, the total count (count rate) of X-ray signals per unit time of the counters 4 is represented by "$C_{tot}$", In addition, the count (count rate) at a given pulse height $V_n$, which is a pulse height analysis result, is represented by "$c(V_n)$", and the count (count rate) at a given threshold pulse height $V_n$, which is a threshold analysis result, is represented by "$C(V_n)$". The count rate calculator 62 uses the total count "$C_{tot}$" to calculate the count rate "$C(V_n)$" of the X-ray signals at pulse heights equal to or higher than the given threshold by the following Equation (1):

$$C(V_n) = C_{tot} - \sum_{i=0}^{n} c(V_i) \qquad (1)$$

The pulse height frequency distribution generator 63 calculates the difference between the count rate "$C(V_n)$" calculated by Equation (1) and the count rate "$C(V_{n-1})$" by the following Equation (2) to obtain a count rate "$c(V_n)$", which is the count at the given pulse height $V_n$ as the pulse height analysis result. Thus, the pulse height frequency distribution generator 63 calculates the count rate for each threshold by detecting the difference in the count rate between the thresholds, to generate a pulse height frequency distribution.

$$C(V_{n-1}) = C(V_n) = \left(C_{tot} - \sum_{i=0}^{n-1} c(V_i)\right) - \left(C_{tot} - \sum_{i=0}^{n} c(V_i)\right) = c(V_n) \qquad (2)$$

Figure 8:
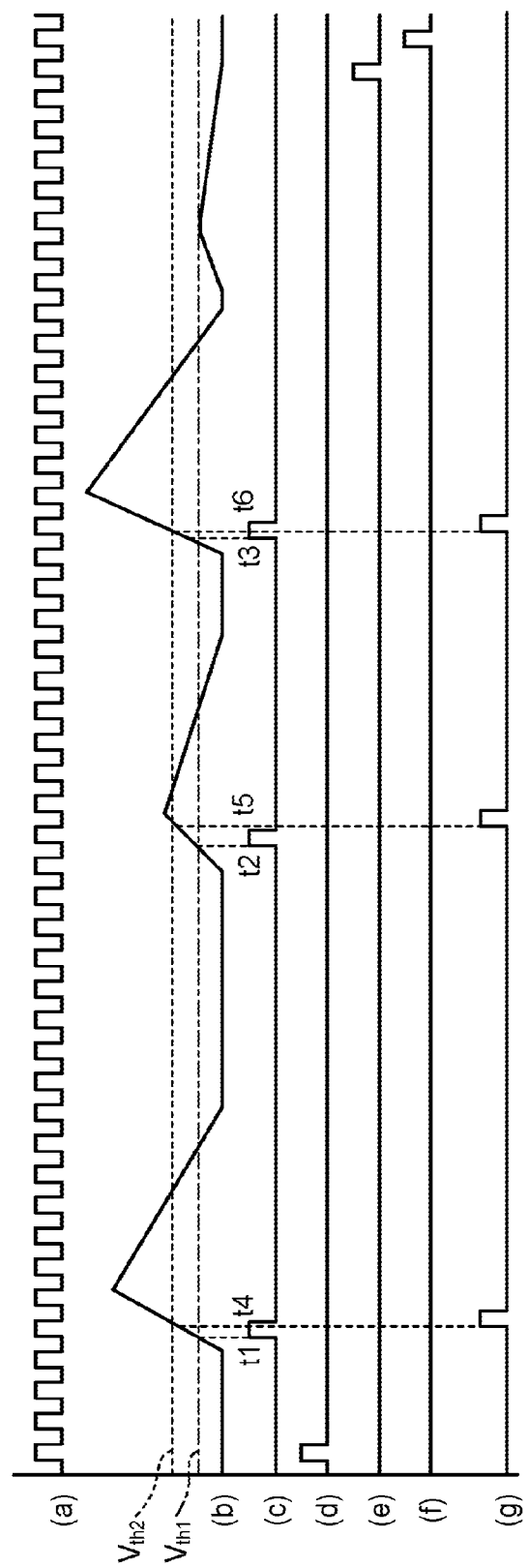
FIG. 8 is a timing chart illustrating waveforms at respective components of the photon counting CT system of the first embodiment.

FIG. 8 illustrates a timing chart of waveforms of X-ray signal counting operations at the respective components. A waveform represented by a symbol (a) in FIG. 8 is the waveform of a system clock. A waveform represented by a symbol (b) in FIG. 8 is the waveform of an X-ray signal output from the TIA 2. A level represented by a dotted line on the waveform represented by the symbol (b) in FIG. 8 is an example level of the thresholds $V_{th1}$ and $V_{th2}$ changed by the threshold controller 61. A waveform represented by a symbol (c) in FIG. 8 is the waveform of pulses output from the comparators 3 when the level of an X-ray signal exceeds the threshold $V_{th1}$.

A waveform represented by a symbol (d) in FIG. 8 is the waveform of a pulse (start pulse) indicating a count start of a count time of pulses output from the comparators 3. A waveform represented by a symbol (e) in FIG. 8 is the waveform of a pulse (end pulse) indicating a count end of a count time of pulses output from the comparators 3. A period between the start pulse and the end pulse corresponds to one detection interval during which pulses output from the comparators 3 are counted. This one detection interval is determined in advance by the number of system clocks. In addition, the number of system clocks is changeable by the CPU 50 according to the radiation measurement program.

A waveform represented by a symbol (f) in FIG. 8 is the waveform of an update pulse indicating a timing for updating the thresholds by the threshold controller 61. A waveform represented by a symbol (g) in FIG. 8 is the waveform of pulses output from the comparators 3 when the level of an X-ray signal exceeds the threshold $V_{th2}$.

The counters 4 count the numbers of pulses output from the comparators 3 when the level of an X-ray signal exceeds the threshold $V_{th1}$ as illustrated at times t1, t2, and t3 of the waveform represented by the symbol (c) in FIG. 8 during a first detection interval from a start pulse until an end pulse. After one detection interval is terminated, the threshold supplied to the comparators 3 is updated from the threshold $V_{th1}$ to the threshold $V_{th2}$ by an update pulse. The counters 4 then count the numbers of pulses output from the comparators 3 when the level of an X-ray signal exceeds the threshold $V_{th2}$ as illustrated at times t4, t5, and t6 of the waveform represented by the symbol (g) in FIG. 8 during a second detection interval from the next start pulse until the next end pulse.

When the number of pulses (=pulses output from the comparators 3) of an X-ray signal exceeding a threshold counted from a start pulse until an end pulse is represented by "n" and the number of pulses of a system clock is represented by "n<CLK>," the count rate "Cps" satisfies a relation of "Cps∝n/n<CLK>," and thus the frequency of occurrence of pulses can be estimated by calculation of pulse equivalent per unit time (unit clock). In the case of the photon counting type detector 13 for use in CTs, the count rate of X-ray photons is as high as $10^6$-$10^8$ 1/s (a sufficient amount of X-rays are incident on the detector 13 even in a short time), which provides sufficient statistical precision even in a short time.

Although data are acquired at a sufficient count rate, however, the data contain statistical error in counting photons. The photon counting CT system of the embodiment thus reduces the statistical error contained in the acquired data before processing the data. Hereinafter, a "calibration mode" in which a measurement result is calibrated and an "actual measurement mode" in which an image is actually constructed with use of measurement data will be described.

First, FIG. 9 is a flowchart illustrating a process flow in the measurement calibration mode. In the measurement calibration mode, in step S1, data output by the detector 13 and a readout circuit coefficient processor are acquired by a FPGA (Field Programmable Gate Array) provided subsequent thereto. The FPGA outputs the acquired data in a form of a data string of a combination of a measurement signal threshold (Vth_1, Vth_2, Vth_3, . . . ) and a count rate (count/(number of clocks): Count Rate_, Count Rate_ 2, . . . ) as illustrated in FIG. 10. The FPGA thus outputs a data string such as "Vth_, Count Rate_1", "Vth_2, Count Rate_2", . . . , for example.

Figure 11:
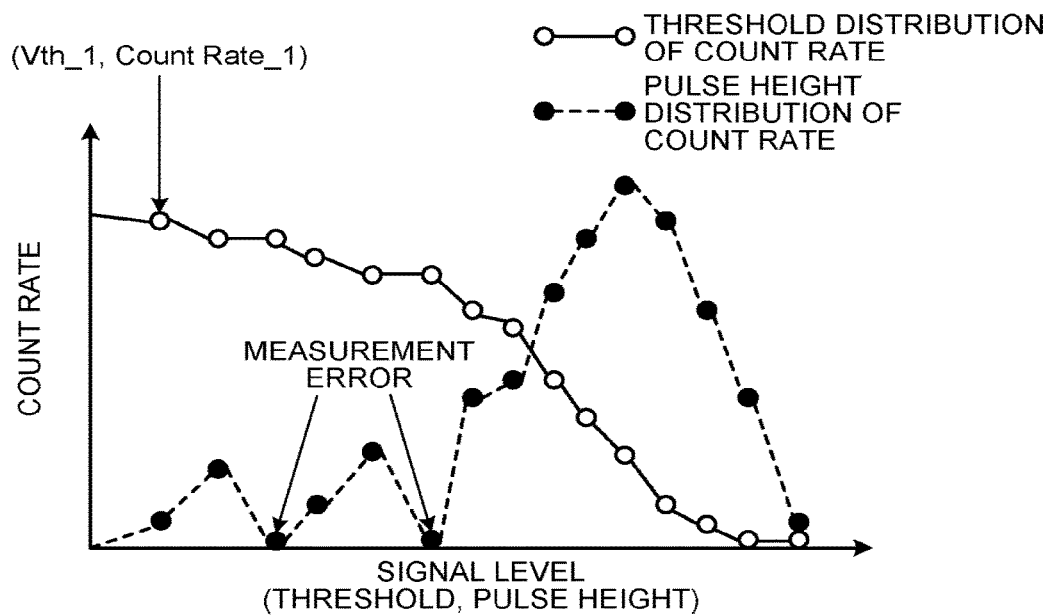
FIG. 11 is a graph illustrating an example of a pulse height distribution of the count rate, in which a threshold distribution of the count rate and noise are superimposed on each other.

Subsequently, in step S2, the CPU 50 (see FIG. 3) of the console 30 provided subsequent to the FPGA acquires the data string output from the FPGA, and displays a threshold distribution of the count rate illustrated by a graph of white dots in FIG. 11 and a pulse height histogram calculated by computation with each threshold illustrated by black dots in FIG. 11. At this point, the data string contains noise caused by the measurement error, which causes discontinuities or unavailabilities of data as illustrated in FIG. 11.

In step S3, the CPU 50 thus applies smoothing to the threshold distribution of the count rate to calculate a parameter by which the noise is reduced. The CPU 50 saves the calculated parameter for use in the "present measurement mode", which will be described below. Note that such a process in the "measurement calibration mode" is performed before product shipment or during operation check, for example. Such a process in the "measurement calibration mode" need not be performed each time the apparatus is started, but may be performed each time the apparatus is started.

Figure 12:
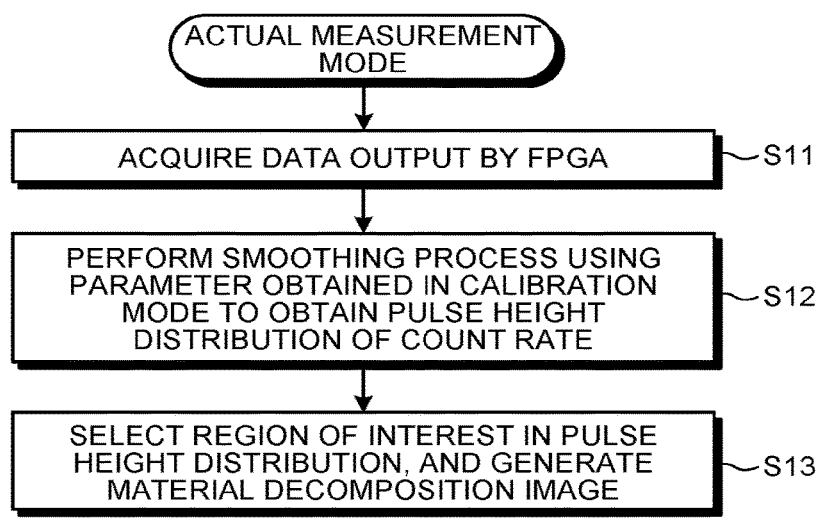
FIG. 12 is a flowchart illustrating a process flow in an actual measurement mode.
Figures 13, 14:
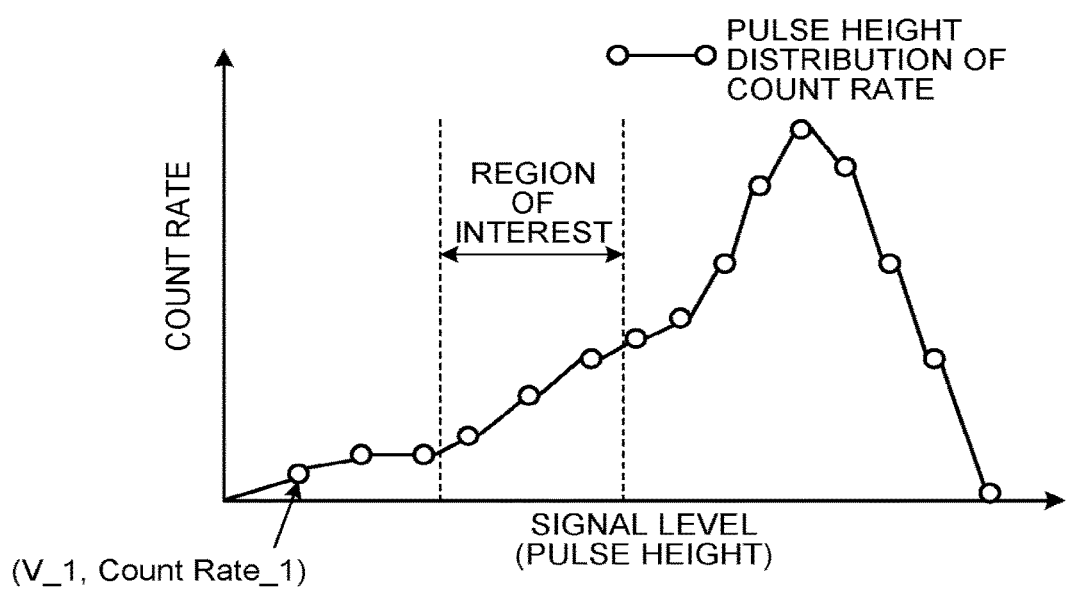
FIG. 13 is a table illustrating an example of noise-reduced data strings.
FIG. 14 is a graph illustrating a count rate pulse height distribution generated with use of a noise-reduced data string.

Next, the flowchart of FIG. 12 is a flowchart illustrating a process in the "actual measurement mode". In the actual measurement mode, the FPGA acquires data output from the detector 13 and the readout circuit coefficient processor in step S11. In step S12, the FPGA performs a smoothing process using the parameter calculated in the calibration mode to output the noise-reduced data string (V_1, Count Rate_1) as illustrated in FIG. 13. The CPU 50 uses the noise-reduced data string to obtain the pulse height distribution of the count rate as illustrated in FIG. 14. In step S13, the CPU 50 then acquires the data output from the FPGA, selects a signal level of a part corresponding to a region of interest (ROI) set in the pulse height distribution of the count rate as illustrated in FIG. 14, and obtains a material decomposition image or the like through image processing. In this manner, a noise-reduced material decomposition image or the like can be obtained.

As is clear from the description above, the photon counting CT system of the first embodiment is provided with one comparator 3 for output pulses of the detector 13, and is configured to update the thresholds of the comparators 3 at every measurement time to measure the frequencies of occurrence of pulses with the thresholds and generate a pulse height frequency distribution of outputs of a photon detector in response to radiation incidence. This allows the area of the detector necessary for pulse height analysis to be significantly reduced, and power consumption to be reduced.

Second Embodiment

Next, a photon counting CT system of a second embodiment will be described. The case of the first embodiment described above is an example in which one comparator 3 is provided for output pulses of the detector 13. In contrast, in the second embodiment, two comparators are provided for output pulses of the detector 13. Note that the first embodiment and the second embodiment are different from each other only in this regard. Thus, only the difference therebetween will be described below, and the same description will not be repeated.

Figure 15:
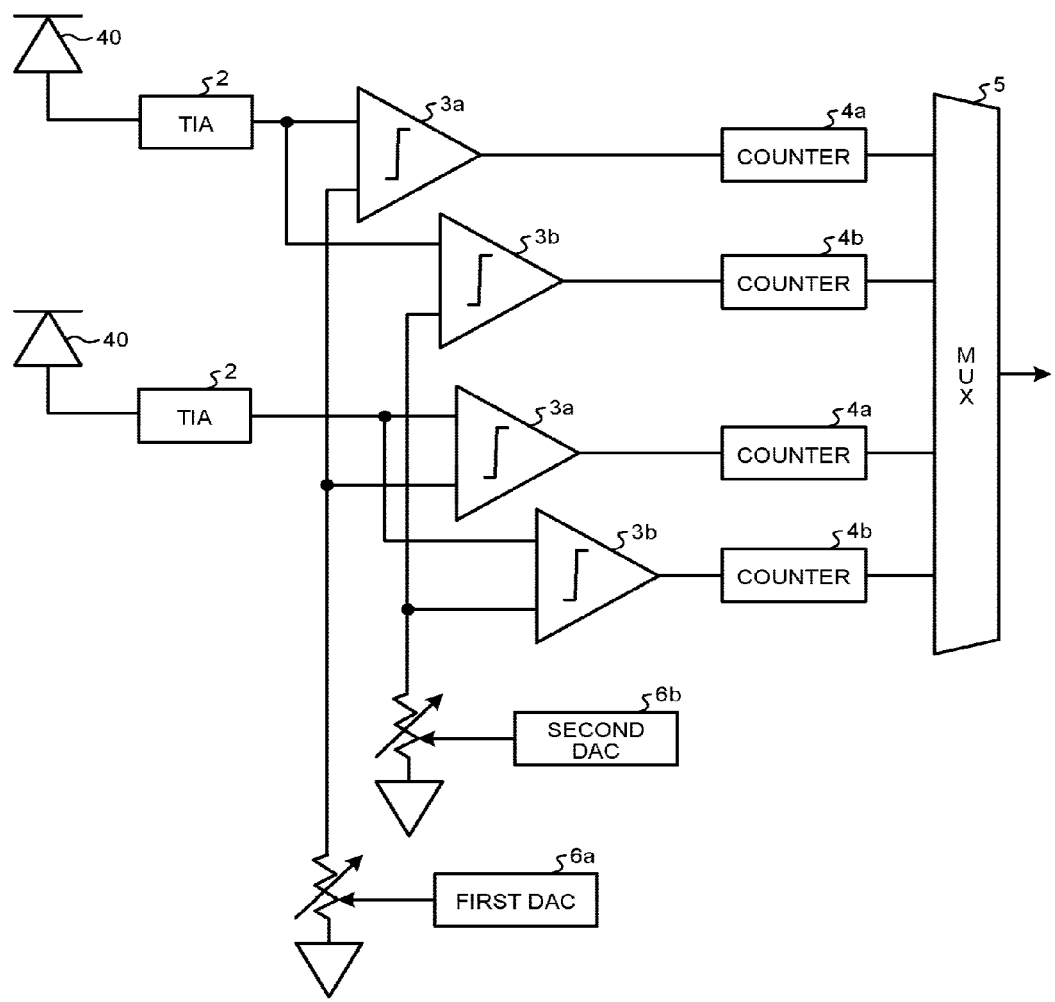
FIG. 15 is a block diagram of an analog front end of a detector provided in a photon counting CT system of a second embodiment.

FIG. 15 is a block diagram of an analog front end provide at an output of the detector 13 of the photon counting CT system of the second embodiment. As illustrated in FIG. 15, in the case of the photon counting CT system of the second embodiment, two comparators 3a and 3b, for example, are provided for the output pulses of each of the detecting elements 40 of the detector 13. Alternatively, three or more comparators may be provided. As a result of providing the comparators 3a and 3b, a counter 4a for counting pulses from the comparator 3a and a counter 4b for counting pulses from the comparator 3b are provided.

Furthermore, in the photon counting CT system of the second embodiment, a first threshold (see $V_{th1}$ of the waveform represented by the symbol (b) in FIG. 8) is supplied from a first DAC 6a to the comparator 3a, a second threshold (see $V_{th2}$ of the waveform represented by the symbol (b) in FIG. 8) is supplied from a second DAC 6b to the comparator 3b. Thus, in the photon counting CT system of the second embodiment, the comparator 3a, the counter 4a, and the first DAC 6a perform counting of X-ray signals using the first threshold, and in parallel with this, the comparator 3b, the counter 4b, and the second DAC 6b perform counting of X-ray signals using the second threshold. Note that the threshold controller 61 controls update of the thresholds to supply a third threshold to the comparator 3a via the first DAC 6a and a fourth threshold to the comparator 3b via the second DAC 6b at the timing of the above-described update pulse (see the waveform represented by the symbol (f) in FIG. 8).

Since the photon counting CT system of the second embodiment as described above counts X-ray signals in parallel using different thresholds, the detection speed is increased and the same effects as those of the first embodiment described above are achieved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray measuring apparatus comprising:
    a detector including a plurality of detecting elements each configured to convert energy of an incident X-ray into a first electrical signal;
    a plurality of comparators corresponding to the respective detecting elements, each comparator being configured to output a second electrical signal when a level of the corresponding first electrical signal is higher than or equal to a threshold;
    a threshold controller configured to supply a first value as the threshold to the respective comparators at a first time, and supply a second value as the threshold to the respective comparators at a second time different from the first time;
    a plurality of counters corresponding to the respective comparators, each counter being configured to count the corresponding second electrical signal; and
    a pulse height frequency distribution generator configured to generate a pulse height frequency distribution of the X-ray by using counts of the counters.

2. The apparatus according to claim 1, further comprising a count rate calculator configured to calculate a count rate for each of the thresholds, the count rate being obtained by dividing the count by a measurement time of the X-ray, and calculate a difference between the count rates for the thresholds, wherein
    the pulse height frequency distribution generator uses the difference between the count rates to generate a pulse height frequency distribution of the X-ray.

3. The apparatus according to claim 1, wherein
    a plurality of the comparators and a plurality of the counters are provided for a detection output of each one of the detecting elements, and
    the threshold controller sets different thresholds for the comparators.

4. A computer program product comprising a non-transitory computer-readable medium containing a program, wherein the program, when executed by a computer, causes the computer to execute:
    outputting, by each of a plurality of comparators corresponding to a plurality of detecting elements each configured to convert energy of an incident X-ray into a first electrical signal in a detector, a second electrical signal when a level of the corresponding first electrical signal is higher than or equal to a threshold;
    supplying a first value as the threshold to the respective comparators at a first time;
    supplying a second value as the threshold to the respective comparators at a second time different from the first time;
    counting, by each of a plurality of counters corresponding to the respective comparators, the corresponding second electrical signal; and
    generating a pulse height frequency distribution of the X-ray by using counts of the counters.

5. The computer program product according to claim 4, wherein the program further causes the computer to execute:
    calculating a count rate for each of the thresholds, the count rate being obtained by dividing the count by a measurement time of the X-ray; and
    calculating a difference between the count rates for the thresholds, wherein
    the difference between the count rates is used to generate a pulse height frequency distribution of the X-ray.

6. The computer program product according to claim 4, wherein
    a plurality of the comparators and a plurality of the counters are provided for a detection output of each one of the detecting elements, and
    the program further causes the computer to execute setting different thresholds for the comparators.

7. An X-ray computed tomography apparatus comprising:
    an irradiator configured to emit an X-ray;
    a detector including a plurality of detecting elements each configured to convert energy of an incident X-ray into a first electrical signal;
    a plurality of comparators corresponding to the respective detecting elements, each comparator being configured to output a second electrical signal when a level of the corresponding first electrical signal is higher than or equal to a threshold;
    a threshold controller configured to supply a first value as the threshold to the respective comparators at a first time, and supply a second value as the threshold to the respective comparators at a second time different from the first time;

a plurality of counters corresponding to the respective comparators, each counter being configured to count the corresponding second electrical signal;

a pulse height frequency distribution generator configured to generate a pulse height frequency distribution of the X-ray by using counts of the counters; and a reconstructor configured to reconstruct an X-ray computed tomography image by using the pulse height frequency distribution of the X-ray.

* * * * *